United States Patent [19]

Haber et al.

[11] Patent Number: 5,116,613
[45] Date of Patent: May 26, 1992

[54] ANTIBODY-THROMBOLYTIC AGENT PRODUCT AND METHOD OF USE

[75] Inventors: Edgar Haber, Weston; Gary R. Matsueda, Winchester, both of Mass.

[73] Assignee: The General Hospital Corporation, Boston, Mass.

[21] Appl. No.: 689,851

[22] Filed: Jan. 8, 1985

[51] Int. Cl.$^5$ ............... A61K 39/395; C07K 15/28
[52] U.S. Cl. ............... 424/85.8; 435/70.21; 435/172.2; 435/240.27; 435/188; 435/212; 435/215; 435/216; 530/388.25; 530/391.7; 530/387.9
[58] Field of Search ............ 424/85, 9, 177, 85.8; 435/68, 172.2, 240, 188, 215, 216, 212, 68.1, 70.21, 240.27; 530/387-388; 935/105, 107

[56] References Cited

U.S. PATENT DOCUMENTS 4,147,765 4/1979 Stephan et al. ............... 424/85.8
4,245,040 1/1981 Pilgeram ............... 435/13

FOREIGN PATENT DOCUMENTS 2538784 9/1984 Australia.
3487284 3/1985 Australia.
0146050 6/1985 European Pat. Off..

OTHER PUBLICATIONS

Pacella, B. L. et al., Molecular Immunol., vol. 20(5):521–528 (1983) cited in Bio. Abstract 7606,9866.
Gaffney, P. J. et al., Haemostasis 10(6):304–311 (1981) cited in Bio. Abstract 74012197.
DeProst, D. et al., Thromb. Haemostasis. 50(4):792–796 (1983) cited in Bio. Abstract 78005612.
Hui et al., Thrombosis and Haemostasis, 54(2):524–527 (1985).
Carrasquillo et al., Radioimmunodetection of Human Melanoma with Monoclonal Antibodies, in Radioimaging and Radioimmunotherapy, Burchiol et al., eds, Elsevier Science, 1983.

Primary Examiner—John Doll
Assistant Examiner—Robert D. Budens
Attorney, Agent, or Firm—Sterne, Kessler, Goldstein & Fox

[57] ABSTRACT

A thrombolytic product comprising a fibrin-specific antibody substantially devoid of fibrinogen cross-reactivity coupled to a thrombolytic agent.

8 Claims, 2 Drawing Sheets

ANTIBODY-THROMBOLYTIC AGENT PRODUCT AND METHOD OF USE

BACKGROUND OF THE INVENTION

1. Field of the Invention

The present invention relates to therapeutic products obtained by coupling antibodies to thrombolytic agents, as well as methods for using the same to dissolve blood clots.

2. Brief Description of the Background Art

Coronary arteriographic studies indicate that 90-95% of transmural myocardial infarctions are caused by coronary thrombosis (DeWood, M. A. et al., N. Eng. J. Med., 303:897–902 (1983)). Although thrombolytic agents currently available can lyse coronary artery thrombi in the early hours of coronary thrombosis and thereby diminish myocardial injury, their clinical application has been attended by significant problems. These agents are activators for the precursor plasminogen, activating the same to the fibrinolytic enzyme plasmin. Plasmin is non-selective and not only effects lysis of the fibrin in the thrombus, but also promotes generalized fibrinogenolysis, at times resulting in severe bleeding (Laffel, G. L. et al., ibid, 311:710–717 and 770–776 (1984)). Human tissue plasminogen activator may be more fibrin-specific, but bleeding complications have nevertheless been observed.

Currently, two activators are commercially available, streptokinase and urokinase. Both are indicated for the treatment of acute cardiovascular disease such as infarct, stroke, pulmonary embolism, deep vein thrombosis, peripheral arterial occlusion, and other venous thromboses. Collectively, these diseases account for major health hazards and risks. Strep-tokinase and urokinase, however, have severe limitations. Neither has a high affinity for fibrin; consequently, both activate circulating and fibrin-bound plasminogen relatively indiscriminately. The plasmin formed in circulating blood is neutralized rather quickly and lost for useful thrombolyses. Residual plasmin will degrade several clotting factor proteins, for example, fibrinogen, factor V and factor VIII, causing hemorrhagic potential. In addition, streptokinase is strongly antigenic and patients with high antibody titers respond inefficiently to treatment and cannot remain on continuous treatment. The recent availability of human tissue-type plasminogen activator has somewhat improved the therapeutic prospects. Nevertheless, the issue of selectivity remains an important one.

SUMMARY OF THE INVENTION

In order to increase the selectivity of thrombolytic agents, the inventors have conceived and developed powerful and selective complex thrombolytic products. These products are obtained by providing:

a fibrin-specific antibody substantially devoid of fibrinogen cross-reactivity coupled to a thrombolytic agent.

The invention also relates to methods of lysing a thrombus by bringing said thrombus in contact with a lysing amount of the antibody/thrombolytic product mentioned above.

Pharmaceutical compositions comprising the product together with pharmacologically appropriate carriers are also included in this invention.

BRIEF DESCRIPTION OF THE PREFERRED EMBODIMENTS

Figure 1:
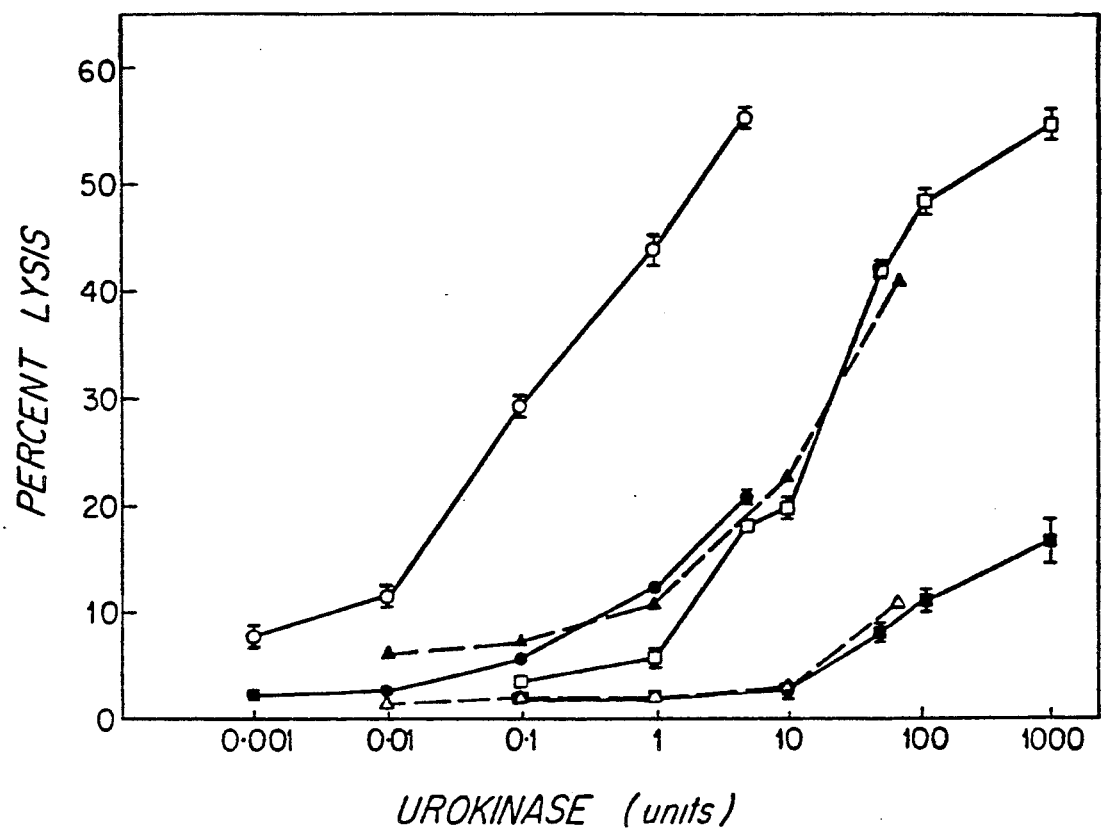
FIG. 1 shows the release of labeled peptides from fibrin-Sepharose by a conjugate of urokinase and fibrin-specific antibody (●, 2.5 hours; ○, 15 hours), urokinase myosin antibody conjugate (△, 2.5 hours; ▲, 15 hours), and unconjugated urokinase (■, 2.5 hours; □, 15 hours). Conjugated or unconjugated urokinase (100 ul containing the indicated amount of urokinase) were incubated for 4 hours with 100 ul $^{125}$I fibrin-Sepharose, washed with 1×3 ml 0.1M Tris, 0.1M NaCl, 0.5% BSA, 0.5% Triton ×100 and 3×3 ml TBSA, and incubated for 2.5 and 15 hours with purified plasminogen (120 mg/l). Lysis was expressed as the quotient of released radioactivity and total radioactivity. Each point represents the mean standard ± deviation of three independent determinations.

The antibodies usable in preparing the products of the present invention may be any antibodies which are fibrin-specific and are substantially devoid of fibrinogen cross-reactivity. For example, antibodies with that specificity have been described in Hui, K. Y. et al., Science, 222:1129–1131 (1983). Further description of the same type of antibodies can be found in commonly assigned co-pending U.S. patent application Ser. No. 603,155, filed Apr. 23, 1984, by Gary R. Matsueda et al. for "Fibrin-Specific Monoclonal Antibodies Lacking Fibrinogen Cross-Reactivity," the entire contents of which are herein incorporated by reference.

The aforementioned co-pending patent application, for example, describes antibodies and methods of preparing the same of the specificity desired in the present invention, by providing peptides capable of raising such antibodies. These peptides generally are those comprising the formula:

$H_2N\text{-A-B-C-D-E-F-G-COR}^1$ wherein A is glycine, B is histidine or proline, C is arginine, D is proline or valine, E is leucine or valine, F is aspartic acid or glutamic acid, and G is lysine or arginine;

$R^1$ is $R^2$; lys-CO-$R^2$; -lys-arg-CO-$R^2$ or -lys-arg-glu-CO-$R^2$;

$R^2$ is -cys-COR$^3$, OH, OM, or NR$^4$R$^5$;

$R^3$ is OH, OM, or NR$^4$R$^5$;

M is a pharmaceutically acceptable cation or a lower branched or unbranched alkyl group; $R^4$ and $R^5$ are the same or different and are selected from the group consisting of H or a lower alkyl group.

These peptides, which are only given herein as illustration and are not the only ones which can be used in this invention, are 7-11 peptides and are utilized in sensitization and/or immunization, cell fusion, ascites production, selection of mixed hybridomas and/or subcloning of hybridomas to produce polyclonal monospecific or monoclonal antibodies. The peptides, which contain fibrin-specific sequences, are attached to an immunogenic protein through a connecting bridge, such as maleimidobenzoylated (MB)-keyhole limpet hemocyanine (KLH). Immunized animals or cells obtained therefrom can be used as a source to obtain monospecific antibodies followed by subsequent affinity chromatography using fibrinogen as a ligand, or may be fused to produce hybridomas to secrete anti-fibrin-specific monoclonal antibodies with substantially no cross-reactivity to fibrinogen.

Generally, any antibody obtained by using these or other peptides as immunogens can be utilized. Among the preferred ones are monoclonal antibodies obtained from cell line 59D8 on deposit at the ATCC with Accession No. HB8546, cell line 64C5 on deposit at the ATCC with Accession No. HB8545, and cell line 55D10 on deposit at the ATCC with Accession No. HB8547. These lines were placed on deposit at the American Type Culture Collection (ATCCO), 12301 Parklawn Drive, Rockville, Md., 20852, prior to Apr. 23, 1984.

Other antibodies of the desired specificity are obtained by using as immunogen the amino terminus of the alpha chain of fibrin, or by immunizing with fibrin and then selecting a subset by affinity chromatography using fibrinogen as a ligand.

By the terms "thrombolytic agent" as used in the present specification and claims is meant to include broadly any agent utilized for inducing or initiating the lysis of a thrombus. The most common agents are urokinase, streptokinase and tissue-type plasminogen activator (TPA). Nevertheless, the obtainment of great selectivity observed with the antibodies utilized in the present invention, indicates that any other such thrombolytic agents can be utilized.

The term "couple" as utilized in the specification and claims is meant to include broadly the firm attachment of the thrombolytic agent to the antibody. Such attachment may be covalent or noncovalent, although it is preferably covalent. The coupling of the two entities may be direct or, most commonly, by means of a coupling or conjugating agent. There are several intermolecular cross-linking reagents which can be utilized (see, for example, Means, G. E. and Feeney, R. E., *Chemical Modification of Proteins*, Holden-Day, 1974, pp. 39–43). Among these reagents are, for example, N-succinimidyl 3-(2- pyridyldithio) propionate (SPDP) or N-N'-(1,3-phenylene) bismalemide (both are highly specific for sulfhydryls, and form irreversible linkages); N-N'-ethylene-bis-(iodoacetamide) or other such reagent having 6 and 11 carbon methylene bridges (relatively specific for sulfhydril groups); 1,5-di-fluoro-2,4-dinitrobenzene (forms irreversible linkages with amino and tyrosine groups); p,p'-difluoro-m-m'-dinitrodiphenylsulfone (forms irreversible cross-linkages with amino and phenolic groups); dimethyl adipimidate (specific for amino groups); phenyl-2,4-disulfonylchloride (reacts principally with amino groups); hexamethylenediisocyanate or diisothiocyanate, or azophenyl-p-diisocyanate (reacting principally with amino groups); glutaraldehyde (reacting with several different side chains) and bis-diazobenzidine (reacting primarily with tyrosine and histidine). These are only a few of several cross-linking agents that can be utilized.

The conditions and concentrations useful for obtaining the antibody/thrombolytic agent couples of the invention can be readily adjusted by those of skill in the art by reference to known literature or by no more than routine experimentation.

The molar ratio of thrombolytic agent to antibody can vary from 1:10 to 100:1, preferably 1:1 to 100:1.

The coupled products of the invention can be formulated in appropriate pharmaceutical compositions by including thrombolytic amounts of the desired product together with pharmacologically appropriate carriers. Generally speaking, these carriers include aqueous or alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's, dextrose, and the like. Preservatives and other additives can also be present, such as, for example, antimicrobials, antioxidants, chelating agents, inert gases, and the like. See, generally, *Remington's Pharmaceutical Sciences*, 16th Ed., Mack, eds. 1980.

The coupled products of the invention can be administered to any patient in need of thrombolytic therapy. The administration can be by any appropriate mode, including parenteral, intravenous, intramuscular, intraperitoneal, or, also appropriately, by direct infusion with a catheter, such as in intracoronary administration. The dosage and frequency of administration will depend on the age, sex and condition of the patient, concurrent administration of other drugs, counter indications and other parameters to be taken into account by the clinician.

The dosages and frequency of administration can be comparable to those used for the thrombolytic agents in the prior art. Generally, however, the dosage will be from about 0.001 to 0.2 times the dosage normally utilized for the thrombolytic agents by themselves.

For example, for the urokinase/antibody complex, the administration for systemic fibrinolysis (pulmonary embolism) values for a 75 kilogram person will be:
1. Loading dose: broad range: 150 to 66,000 units over 10 minutes; intermediate range: 330 to 30,000 units over 10 minutes.
2. Maintenance dose: broad range: 187.5 to 66,000 units per hour for 12 to 24 hours; intermediate range: 330 to 37,500 units per hour for 12 to 24 hours resulting in 2,400–1,650,000 total units (Sharma et al., *NEJM*, 306:1268-1276 (1982).

For the urokinase/antibody complex, the intracoronary administration dosage will be:
1. No loading dose.
2. 6–1,200 units per minute for 60–120 minutes resulting in a total of 360–144,000 units solution of 1.5–300 units per ml (Tennant et al., *Circulation*, 69:756-760 (1984)).

For the streptokinase/antibody complex, the systemic intracoronary administration dosage will be:
1. Loading dose: 250–50,000 units.
2. Maintenance dose: 100–20,000 units per hour for 24 hours or boluf injection of 5,000–300,000 units over 30 to 60 minutes.

For the streptokinase/antibody complex, the intracoronary administration dosage will be:
1. Loading dose: 0.01–6,000 units in 3 ml 5% dextrose over 2 minutes.

2. Maintenance dose: 5–1,000 units in one ml 5% dextrose up to maximal dose (500 to 100,000 units) (Laffel and Braunwald, *NEJM*, 311: 710–717 (1984)).

In the aforementioned dosage descriptions, the term "units" refers to the known and established definitions utilized for the activity of the thrombolytic agents in the prior art.

Having now generally described this invention, the same will be better understood by reference to one or more specific examples. These examples are included herein for purposes of illustration only and are not intended to be limiting unless otherwise specified.

EXAMPLE 1

A. Preparation of Urokinase-Antibody Conjugate

Reduced urokinase was coupled to fibrin-specific monoclonal antibody 64C5 via its intrinsic sulfhydryl groups utilizing N-succinimidyl 3-(2-pyridyldithio) propionate (SPDP) groups as a cross-linking agent (Carlsson, J. *et al.*, *Biochem. J.*, 173:723–737 (1978)). SPDP (20 mM in 0.05 ml absolute ethanol) was added to the antibody (6.3 mg in 3.0 ml of 0.01M sodium phosphate, 0.1M NaCl, pH 7.4 (PBS)) and the mixture allowed to react for 30 minutes at room temperature. The solution was subsequently dialyzed against three one-liter changes of PBS. Analysis for 2-pyridyldisulfide content (Grassetti, D. R. and Murray, J. F., *Archives of Biochemistry and Biophysics*, 119:41–49 (1967) and Stuchbury, T. *et al.*, *Biochem. J.*, 151:417–432 (1975)) showed 10.8 residues per antibody molecule. Urokinase (7 mg, 3.5 mg/ml in 0.1M sodium acetate, 0.1M NaCl, pH 4.5) was trace-labeled by addition of 20 uCi 125-I urokinase (0.03 mg in 0.3 ml PBS containing 0.03% NaN$_3$ (PBSA) (Greenwood, F. C. *et al.*, *Biochem. J.*, 89:114–123 (1963)). The mixture was reduced by addition of 0.23 ml 1.0M dithiothreitol in 0.1M sodium acetate, 0.1M NaCl, pH 4.5, for 30 minutes at room temperature and desalted on Sephadex G 25 (0.7×25 cm) equilibrated with PBSA pH 4.5. Peak fractions from the column were pooled (4.3 ml, containing 1.1. mg/ml protein (Lowry, O. H. *et al.*, *J. Biol. Chem.*, 193:265–275 (1951) and mixed with PDP-antibody (2.9 ml, containing 2.1 mg/ml protein (ibid)). The mixture was neutralized and allowed to react overnight. Under these conditions, the intrinsic sulfhydryl groups of the urokinase chains react with the pyridyldisulfide groups of the modified antibody, resulting in displacement of thiopyridine and formation of disulfide-containing intermolecular bridge.

Unconjugated urokinase and its component subunits were separated from the urokinase-antibody conjugate (125 I-UK)-SS-(64C5) by gel filtration on Sephacryl S-200 (2.5×90 cm). Two radioactive fractions were clearly resolved. The first contained the antibody-urokinase conjugate and was free of unconjugated urokinase. By SDS-PAGE, its molecular size exceeded 150 KD and it proved to be radioactive on subsequent autoradiography, indicating that it contained the urokinase subunit. The incorporation of urokinase averaged one mole per 3 of antibody as determined by specific radioactivity of the urokinase subunit. Further evidence of the association of urokinase activity with antibody was obtained by affinity chromatography of the antibody-urokinase conjugate on a column constructed by coupling a synthetic amino terminal beta chain fibrin peptide (Gly-His-Arg-Pro- Leu-Asp-Lys-Cys (Hui, K. Y. *et al.*, *Science*, 222: 1129–1131 (1983)) (BPEPTIDE) to Lysine-Sepharose CL-4B (Kitagawa, T. and Aikawa, T., *J. Biochem (Japan)*, 79: 233 (1976)). The eluate of this column (0.2M glycine HCl, pH 2.8) was radioactive and fibrinolytic in the assay described below (both properties of urokinase). The same methods were used to synthesize and purify a conjugate of urokinase and myosin-specific monoclonal antibody 3H3 (I-UK)-SS-(3H3) (Khaw, B. A. *et al.*, *Hybridoma*, 3:11–23 (194)).

B. Assay for Fibrinolytic Activity

A quantitative fibrinolytic assay was devised by linking fibrin monomer to Sepharose. Kabi grade L fibrinogen (500 mg) was dissolved in 50 mM phosphate buffer, pH 7.4 and then passed over lysine-Sepharose to eliminate traces of plasminogen. The purified fibrinogen was trace-labeled by the addition of 150 uCi 125-I fibrinogen (IBRIN) and the mixture coupled to 150 ml cyanogen bromide activated Sepharose 4B-Cl. After thorough washing, the gel was suspended in 0.1M Tris, 0.15M NaCl, 0.02% NaN$_3$, pH 7.4 (TBSA) and the immobilized fibrinogen converted to fibrin by addition of human thrombin (1 NIH unit/ml) in the presence of 100 mM CaCl$_2$. After 4 liters of washing, 125-I fibrin-Sepharose was stored in TBSA at 0 degrees. The substituted Sepharose was stable, releasing 0.1% of its radioactivity at 2.5 hours and 2.1% at 15 hours on incubation in the absence of urokinase-containing conjugates.

To assess their relative fibrinolytic activity, increasing amounts of (125 I-UK)-SS-(64C5) and unconjugated urokinase were incubated with 100 ul of 125 I-fibrin-Sepharose for 4 hours. The Sepharose was then washed first with 3 ml of a solution comprising 0.1M Tris, 0,1M NaCl, 0.5% bovine serum albumin and 0.5% Triton X-100 and then with three 3 ml aliquots of TBSA. Thereafter, the resin was incubated at room temperature with purified plasminogen (Deutsch, D. G. *et al.*, *Science*, 170:1095–1096 (1970)) (0.15 mg/ml) in 50 mM phosphate buffer, pH 7.4. After either 2.5 or 15 hours, the mixture was centrifuged and the radio-activity of the supernatant determined in a gamma scintillation counter. This procedure was repeated with (125 I-UK)-SS-(3H3).

In order to obtain kinetic information (125 I-UK)-SS-(3H3), or (125 I-UK)-SS-64C5 in TBSA containing 0.12 mg/ml plasminogen were recirculated over a (0.3×5 cm) column containing 300 ul 125 I fibrin-Sepharose at a rate of 1 ml per minute. At indicated times, three samples of 1 ml each were collected and their radioactivity determined.

Figure 2:
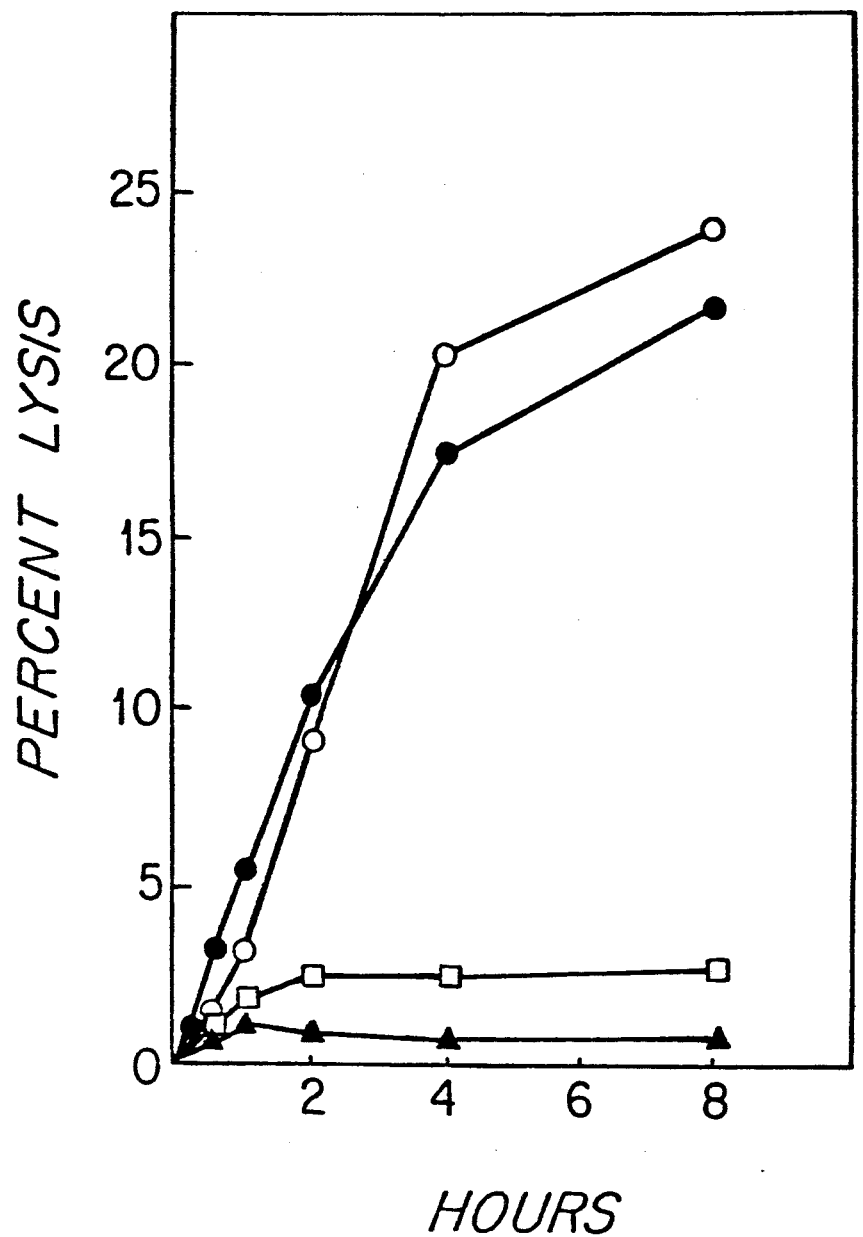
FIG. 2 shows the release of labeled peptides from fibrin-Sephrose during recirculation of a solution containing plasminogen (0.12 mg/ml) and fibrin-specific antibody 64C5 in the presence (○) and absence (●) of 3.5 mg/ml fibrinogen. The experiment was repeated with a myosin-specific antibody (3H3) in the presence (▲) and absence (□) of fibrinogen. In each instance, the recirculating fluid contained 0.25 units of urokinase activity/ml coupled to either of the antibodies. Each point represents the mean of three determinations with a standard deviation of less than 1.6%.

FIG. 1 indicates that the concentration of (125 I-UK)-SS-(64C5) required to release labeled peptides from fibrin-Sepharose was 1/100 of that of unconjugated urokinase. The myosin antibody conjugate (125 I-UK)-SS-(3H3) did not differ significantly from unconjugated urokinase. FIG. 2 shows that (125 I-UK)-SS-(64C5) markedly enhances the rate of release of peptides from fibrin-Sepharose and that this is unimpaired by fibrinogen at a physiologic concentration. BPeptide inhibits fibrinolysis of (125 I-UK)-SS-(64C5), whereas it has no effect on the fibrinolytic rate of unconjugated urokinase or (125 I-UK)-SS-(3H3) (data not shown).

C. Conclusions

A monoclonal antibody specific for fibrin is able to target the plasminogen activator urokinase to fibrin and by virtue of enhanced local concentration, increase the efficiency of plasmin lysis by 100-fold. The antibody is sufficiently fibrin-specific so that physiologic effects of fibrinogen do not interfere with enhanced fibrinolysis. Fibrinolytic effectiveness is not enhanced by coupling of urokinase to a monoclonal antibody of irrelevant specificity but it is markedly diminished by a peptide representing the epitope recognized by the fibrin-specific antibody.

Having now fully described this invention, it will be appreciated that the same can be performed within a wide and equivalent range of parameters, conditions, modes of administration, conjugates, antibodies, fibrinolytic agents, and the like without affecting the spirit or scope of the invention or of any embodiment therein.

What is claimed as new and intended to be covered by Letters Patent of the United States is:

1. A thrombolytic product comprising a fibrin-specific antibody substantially devoid of fibrinogen cross-reactivity coupled to a thrombolytic agent.

2. The product of claim 1 wherein said thrombolytic agent is selected from the group consisting of streptokinase, urokinase, and tissue-type plasminogen activator.

3. The product of claim 1 wherein said thrombolytic agent is urokinase.

4. The product of claim 1 wherein said antibody is a monoclonal antibody.

5. A pharmaceutical composition useful for thrombolysis comprising the product of any of claims 1-4 and an inert physiologically acceptable carrier.

6. The product of claim 1 wherein said thrombolytic agent is tissue-type plasminogen activator.

7. The product of claim 6 wherein said antibody is a monoclonal antibody.

8. The product of claims 4 or 7 wherein said monoclonal antibody is obtained from cell line ATCC HB 8545, HB 8546, or HB 8547.

* * * * *